(12) United States Patent
Hemsendorf et al.

(10) Patent No.: US 8,400,630 B2
(45) Date of Patent: Mar. 19, 2013

(54) METHOD AND DEVICE FOR THE DETECTION OF DEFECTS IN AN OBJECT

(75) Inventors: Marc Hemsendorf, München (DE); Christian Probst, München (DE)

(73) Assignee: GP Inspect GmbH, Neuried (DE)

( * ) Notice: Subject to any disclaimer, the term of this patent is extended or adjusted under 35 U.S.C. 154(b) by 204 days.

(21) Appl. No.: 12/874,516

(22) Filed: Sep. 2, 2010

(65) Prior Publication Data

US 2011/0058161 A1    Mar. 10, 2011

Related U.S. Application Data

(60) Provisional application No. 61/239,583, filed on Sep. 3, 2009.

(30) Foreign Application Priority Data

Sep. 2, 2009   (DE) .......................... 10 2009 039 685

(51) Int. Cl.
*G01N 21/00*   (2006.01)
(52) U.S. Cl. ................................. 356/239.1; 356/239.2
(58) Field of Classification Search .... 356/239.1–239.2, 356/237.1–237.5
See application file for complete search history.

(56) References Cited

U.S. PATENT DOCUMENTS

| 5,196,716 A | * | 3/1993 | Moriya et al. ........... 250/559.46 |
| 6,545,279 B1 |  | 4/2003 | Yoshida et al. |
| 2009/0220864 A1 | * | 9/2009 | Tanabe .............................. 430/5 |

FOREIGN PATENT DOCUMENTS

| DE | 4139094 A1 | 6/1993 |
| DE | 10060900 A1 | 8/2001 |
| EP | 1801569 A2 | 6/2007 |

* cited by examiner

*Primary Examiner* — Michael P Stafira
(74) *Attorney, Agent, or Firm* — Laurence A. Greenberg; Werner H. Stemer; Ralph E. Locher (57) ABSTRACT

A method for detecting defects in an object includes a step of locally illuminating the object by radiating in light having a wavelength to which the object is transparent. Multiply reflected components of the incident light are detected while the detection of directly transmitted components of the incident light is at least partly avoided and the detection of singly reflected components of the incident light is at least partly avoided. Defects are identified by evaluating intensity differences in the detected components of the incident light. There is also disclosed a device for carrying out the method.

20 Claims, 6 Drawing Sheets

METHOD AND DEVICE FOR THE DETECTION OF DEFECTS IN AN OBJECT

CROSS-REFERENCE TO RELATED APPLICATION

This application claims the priority, under 35 U.S.C. §119 (a), of German patent application DE 10 2009 039 685.3, filed Sep. 2, 2009, as well as the benefit, under 35 U.S.C. §119(e), of provisional patent application No. 61/239,583, filed Sep. 3, 2009; the prior applications are herewith incorporated by reference in their entirety.

BACKGROUND OF THE INVENTION

Field of the Invention

The invention relates to a method for detecting defects in an object. The object is thereby locally illuminated by radiating in light having a wavelength to which the object is transparent. The invention also relates to a device for carrying out a method of this type. The device includes a light source for locally illuminating the object with light having a wavelength to which the object is transparent, and a detector for detecting light emitted by the light source.

In the manufacture of products it is typically an object to produce as few rejects as possible. Therefore, it is endeavored to check starting materials or semifinished products for possible faults or defects before the latter are transferred into production. In this way it is possible to prevent such defective starting materials or semifinished products from passing through a production process and thus causing costs and outlay before it is ascertained in a concluding inspection, or even later, that the manufactured product has deficiencies. By way of example, in the fabrication of semiconductor components, in particular of solar cells, silicon wafers are used as starting material. These silicon wafers, having a thickness of up to a few hundred micrometers, are comparatively thin and thus at risk of breaking. In some instances, such silicon wafers already have microcracks or other mechanical impairments when they are transferred into the respective processing process. Since such defects are often very difficult to recognize with the naked eye, attempts are made, inter alia, to transilluminate the silicon wafer with light and to identify possible defects in this way.

It has been found, however, that, in the case of inhomogeneous objects, defects can in some instances only be detected very unreliably since the inhomogeneities present make it more difficult to detect these defects. In the case of multicrystalline semiconductor materials, in particular multicrystalline silicon wafers, the grain structure, for example, makes it more difficult to identify cracks, microcracks, inclusions or the like since it is superimposed on them.

SUMMARY OF THE INVENTION

It is accordingly an object of the invention to provide a method and a device for detecting defects in an object which overcome the above-mentioned disadvantages of the heretofore-known devices and methods of this general type and which addresses the problem of providing a method and a device by means of which defects can be reliably detected in an object.

With the foregoing and other objects in view there is provided, in accordance with the invention, a method for detecting defects in an object, the method which comprises:

locally illuminating the object by irradiating the object with incident light having a wavelength to which the object is transparent;

detecting multiply reflected components of the incident light while at least partly avoiding a detection of directly transmitted components of the incident light and at least partly avoiding a detection of singly reflected components of the incident light; and identifying defects by evaluating intensity differences in the detected components of the incident light.

With the above and other objects in view there is also provided, a device for detecting defects in an object, particularly for carrying out the above-summarized method. The device comprises:

a light source for locally illuminating the object with light having a wavelength to which the object is transparent; and a detector for detecting light emitted by said light source;

wherein said detector and said light source are arranged such that at least one part of an illumination region in which the object can be locally illuminated by said light source and also at least one part of an exit region of directly transmitted light components lie outside a detection region of the detector.

In other words, the method according to the invention provides for illuminating the object by radiating in light having a wavelength to which the object is transparent. Furthermore, the method comprises detecting multiply reflected components of the incident light while at least partly avoiding the detection of directly transmitted components of the incident light and at least partly avoiding the detection of singly reflected components of the incident light. Accordingly, multiply reflected components of the incident light are detected, but at the same time at least a portion of directly transmitted components of the incident light and a portion of the singly reflected components of the incident light are not detected. The defects are subsequently identified by evaluating intensity differences in the detected components of the incident light. In this case, light should be understood to mean, in principle, electromagnetic radiation of any type provided that it has a wavelength to which the object is transparent. Directly transmitted components of the incident light within the meaning of the present invention are those light components which are transmitted through the object without prior reflection. Defect within the meaning of the present invention should not be understood generally to mean crystal defects, which also include grain boundaries, for example, but rather mechanical damage to the object, for example cracks, microcracks, spalling, mechanical strains, or inclusions.

In the object, the incident light, provided that it is then reflected, is largely reflected at the interfaces of the object, that is to say at the top side and underside thereof. Such multiply reflected light components cover comparatively long path lengths within the object compared with directly transmitted or merely singly reflected light components. Information about the inhomogeneous structure of the object, for example about the crystal structure of a multicrystalline semiconductor object, in particular of a multicrystalline silicon wafer, is lost in the process. Instead, the constitution of said interfaces, that is to say the constitution of the surface, is crucial for the detected signals. If the surface is comparatively rough, then the multiple scattering described can be compared with a lambertian emitter. The multiple reflection described can then be regarded as lambertian multiple reflection and brings about a relatively isotropic light locally in the object. The fewer directly transmitted or merely singly reflected light components are detected and the more frequently the detected light was scattered, the greater the extent to which the crystal structure disappears in the detected signals. If the detected signals are converted into an image, then the crystal structure correspondingly recedes to a greater extent in the image impression.

If, by contrast, there is a break, for example, in a multicrystalline semiconductor wafer, then said break forms along the crystal structure prevailing there. The surface of the break can accordingly be assumed to be very smooth, with the result that total reflection takes place at said surface. Incident light which propagates in a direction toward the break is totally reflected, i.e. mirrored, at a mirror plane of the break. Said mirror plane can be oriented in any desired manner, in principle, such that the total reflection at the break brings about a brightening either at the top side or the underside of the silicon wafer. By contrast, a corresponding darkening is formed on that side on which the brightening does not occur. The resulting bright-dark characteristic can be utilized in a corresponding image processing algorithm in order to reliably identify the break. In this case, ultimately the intensity differences in the detected components of the incident light are evaluated and the defects, in particular said break, are identified through that. If, instead of a break, there is an inclusion, for example, in the examined object, then it appears dark against a brighter background and can likewise be identified by means of a suitable image processing algorithm.

Figure 1:
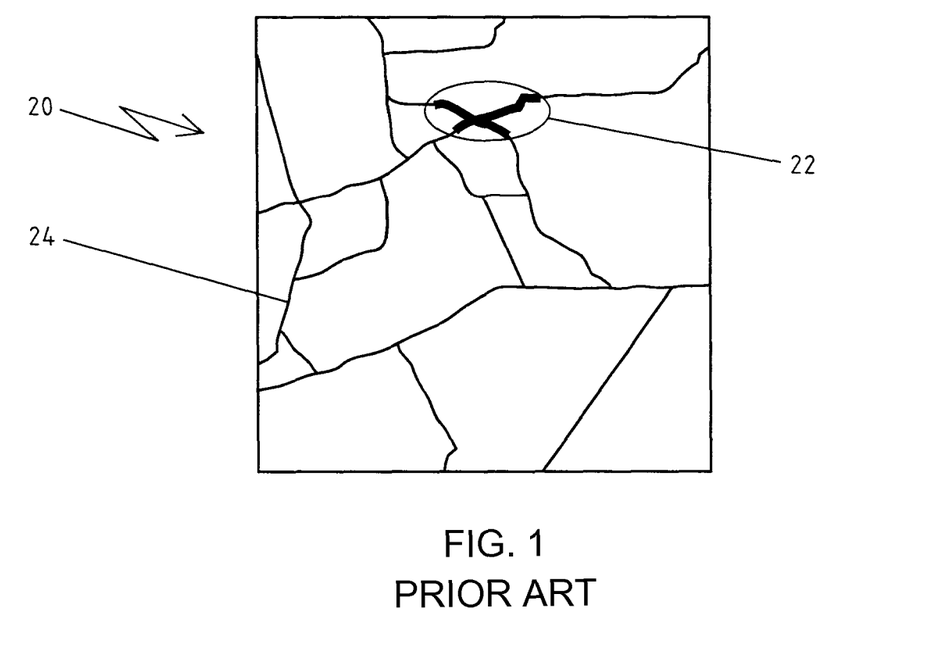
FIG. 1 shows an image of a multicrystalline silicon wafer with a break in schematic illustration, said image being recorded by a method in accordance with the prior art for detecting defects.
Figure 2:
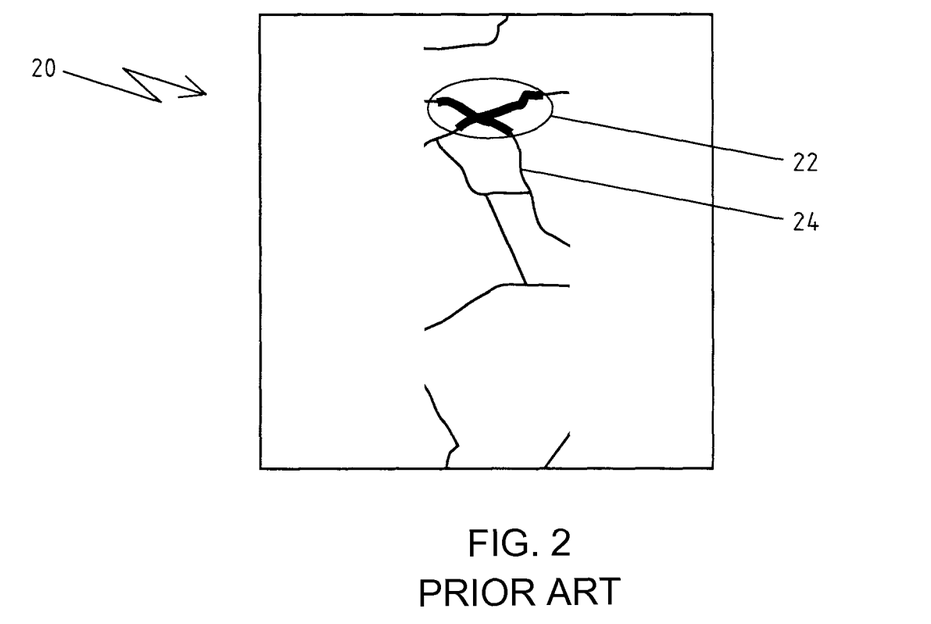
FIG. 2 shows an image of the silicon wafer from FIG. 1 in schematic illustration, said image being recorded by the method according to the invention while partly avoiding the detection of directly transmitted light components and partly avoiding the detection of singly reflected light components.
Figure 3:
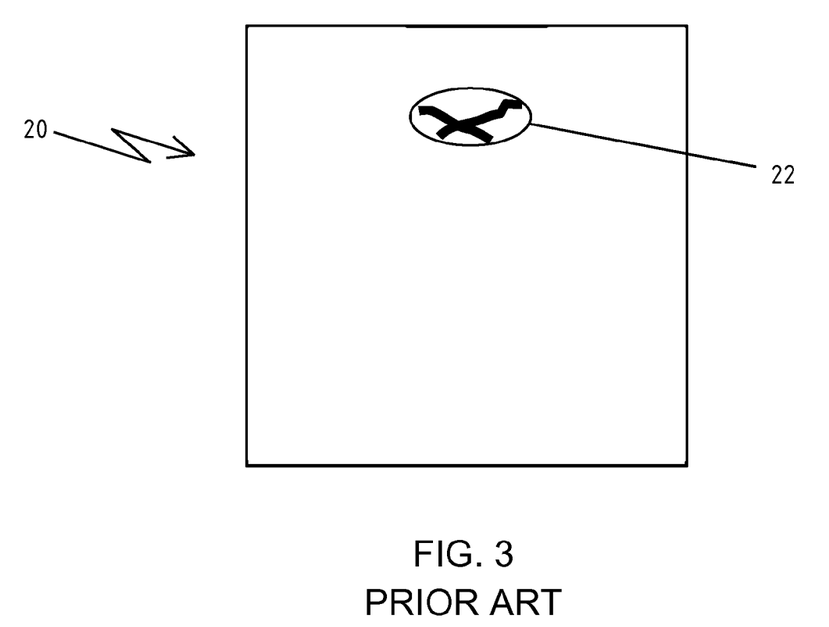
FIG. 3 shows a schematic illustration of an image of the silicon wafer from FIG. 1, said image being recorded by the method according to the invention while completely avoiding the detection of direct light components and completely avoiding the detection of singly reflected light components.

The defects described are illustrated schematically in FIGS. 1 to 3. FIG. 1 shows in schematic illustration an image of a multicrystalline silicon wafer 20 recorded by an infrared camera by means of a direct transmitted-light method in accordance with the prior art. A multiplicity of grain boundaries 24 can be discerned in this image. Breaking surfaces often run along such grain boundaries. Such a break 22 is illustrated in a manner enclosed by a border in FIG. 1. The course of said break is artificially highlighted by thicker line tracing. Without this artificial highlighting, the break 22 would not be able to be distinguished from grain boundaries 24 in practice. It is precisely this which makes it difficult to detect defects in the case of such or similar materials. As already mentioned, the recorded image in FIG. 1 was produced with direct transmitted light. That is to say that the silicon wafer was locally illuminated from one side and primarily the directly transmitted light was detected on the other side by means of the camera. In order to generate a complete image of the silicon wafer 20, the latter was scanned by means of the camera and a light source used.

If, by contrast, as proposed by the methods according to the invention, the detection of directly transmitted light components and the detection of singly reflected light components are at least partly avoided, then an image of the silicon wafer 20 approximately corresponding to the illustration in FIG. 2 can be obtained. As illustrated in this figure, large parts of the grain structure 24 can be masked out in this way, such that the identification of the break 22 occurs significantly more simply. In a vicinity of the break 22, the crystal structure 24 is still discernible in a manner more weakly pronounced than in FIG. 1 since the directly transmitted light components and/or the singly reflected light components are partly detected here.

The grain structure 24 still visible in FIG. 2 can likewise be masked out, however, if the detection of directly transmitted components of the incident light and also the detection of singly reflected components of the incident light are completely avoided. An image like that illustrated in FIG. 3 can be obtained in this case. The break 22 is clearly discernible therein since the grain structure 24 is completely masked out. The image represented schematically in FIG. 3 is then determined by the surface roughness of the silicon wafer 20. It has been found in practice that, to a good approximation lambertian multiple reflection and hence locally isotropic illumination can be realized particularly in the case of multicrystalline silicon wafers 20 that are sawn from a silicon block and overetched using an acidic etching medium.

In one preferred embodiment variant of the method according to the invention, the incident light is focused onto a surface of the object. This enables said object to be illuminated in a very greatly localized manner.

Preferably, for the purpose of illuminating the object, a line light, particularly preferably a line light focused onto the surface of the object, is incident and the multiply reflected components of the incident light are detected along a line. This last can be realized, for example, by means of a linear sensor, in particular by means of a line-type camera.

In one preferred configuration variant of the method according to the invention the defects are detected in inhomogeneous objects. Inhomogeneous objects within the meaning of the present invention should be understood as objects having no uniform basic structure, for example no uniform crystal structure. Multicrystalline objects, in particular multicrystalline semiconductor materials, accordingly constitute such inhomogeneous objects.

In practice, the method according to the invention has proved to be worthwhile in the detection of defects in silicon bodies, preferably in silicon wafers, and particularly preferably in multicrystalline silicon wafers. Silicon wafers within the meaning of the present invention can be, on the one hand, only sawn silicon wafers, sawn and overetched silicon wafers, or else finished or partly processed silicon solar cells.

One development of the invention provides for light having a wavelength of between 1100 and 5000 nm, preferably light having a wavelength of between 1100 and 2000 nm, to be incident during the detection of defects in silicon bodies.

In one preferred configuration variant of the method according to the invention, defects are detected in such silicon bodies which have been sliced from a starting silicon body by sawing. Consequently, the silicon body has at least one surface partly rough from sawing, as a result of which statistical scattering of the incident light can be brought about at the silicon interfaces. The statistics of this scattering can be described comparatively well with those of a lambertian emitter.

If silicon bodies are at least partly overetched before the detection of the defects, then it has been found that, for the detection of defects with the method according to the invention, it is advantageous for the silicon bodies to be overetched using an acidic etching medium. By contrast, overetching using alkaline etching media can make the detection of defects more difficult.

In one configuration variant of the method according to the invention it is provided that for the purpose of locally illuminating, the light is incident on a part of a side of the object and multiply reflected components of the incident light are detected on the same side of the object. This constitutes a so-called reflected-light method. The latter is advantageous particularly when a layer, for example metal coating, impenetrable to the light used is provided on one side of the object, since a light source for the local illumination and also a detector for the detection of multiply reflected light components can then both be arranged on the non-metallized side of the object.

In one advantageous configuration variant, the light is incident obliquely with respect to the surface of the object. As a result of this, the light covers longer path lengths within the object, which has proved to be advantageous for masking out the crystal structure or other inhomogeneities.

In an alternative configuration variant to the reflected-light method described, it is provided that for the purpose of locally irradiating, the light is incident on a part of a first side of the object and multiply reflected components of the incident light are detected on a second side of the object, said second side lying opposite the first side. This procedure is often referred to as a transmitted-light method.

In the case of the transmitted-light method, too, the light is preferably incident obliquely with respect to the surface of the object. This has an advantageous effect on the detection of defects in the manner already described in connection with the reflected-light method.

In one preferred configuration variant of the method according to the invention it is provided that light incident for the purpose of locally illuminating is guided over at least one part of the surface of the object, preferably over a complete side surface of the object. Such guidance can be effected continuously or in scanned fashion. A complete image of the object can be generated in this way. The incident light can be guided over at least one part of the surface of the object by the object being moved relative to a detector and a light source.

The device according to the invention provides a light source for locally illuminating an object with light having a wavelength to which the object is transparent, and also a detector for detecting light emitted by the light source. The detector and the light source are furthermore arranged in such a way that at least one part of an illumination region in which the object can be locally illuminated by means of the light source and also at least one part of an exit region of directly transmitted light components lie outside a detection region of the detector. In this case, the exit region of directly transmitted light components should be understood to mean a surface region of the object in which the directly transmitted components of the incident light emerge from the object. The detection region of the detector denotes that region of the object which can be detected by the detector.

In one configuration variant of the device according to the invention, light having a frequency of between 1100 and 5000 nm, preferably light having a frequency of between 1100 and 2000 nm, can be emitted by means of the light source.

Correspondingly, a detector is preferably provided which is sensitive in the wavelength range of between 1100 and 5000 nm. Particular preference is given to the wavelength range between 1100 and 2000 nm.

In one advantageous configuration variant of the device according to the invention, an optical unit for focusing the light emitted by the light source onto a surface of the object is provided. The light which is emitted by the light source and incident on the object can thereby be localized to a greater extent.

One advantageous configuration variant of the device according to the invention has a transport device, by means of which the object can be transported through the detection region of the detector. A device of this type is preferably designed for continuous operation which is often referred as "inline" operation. In this way, large numbers of objects can be examined in an expedient manner in respect of outlay.

In one preferred embodiment variant, the device according to the invention has an evaluation unit for evaluating intensity differences in the detected components of the incident light.

One development of the invention provides for the detection region of the detector to be spaced apart from the illumination region and from the exit region of directly transmitted light components. In this way, the detection of directly transmitted light components and also the detection of singly reflected light components can largely be avoided in a convenient manner.

In one embodiment variant of the invention, the light source and the detector are arranged on the same side of a mounting plane in which the object can be mounted. This configuration permits the detection of defects in the reflected-light method.

In another embodiment variant, light source and detector are arranged on mutually opposite sides of the mounting plane, which makes it possible to detect defects in the transmitted-light method.

In one preferred configuration variant of the device according to the invention, at least one line-type light source is provided as light source and at least one device with a linear sensor is provided as detector. A line-type camera is preferably used as linear sensor.

In all embodiment variants of the device according to the invention, the detector preferably has an objective that operates in the wavelength range of the light source. In this case, the objective and possible further optical components of the detector are advantageously designed in such a way that the object region situated in the detection region of the detector is imaged onto a sensor of the detector, for example the linear sensor thereof.

In one preferred configuration variant, the linear sensor and a possible objective and possible further optical components are oriented in such a way that an object to be examined, for example a silicon wafer, can be completely detected while it is transported through the detection region of the detector. By transporting the object to be examined, for example the silicon wafer, through the detection region, it is thus possible to create a complete image of the object, for example of the silicon wafer.

One development of the device according to the invention provides for the line-type light source and the linear sensor to be oriented in such a way that a light plane spanned by the longitudinal extension direction of the line-type light source and the optical axis thereof and a detector plane spanned by the longitudinal extension direction of the linear sensor and the optical axis thereof respectively form straight lines of intersection with the mounting plane, said straight lines of intersection being oriented parallel to one another. Since the detector is a linear sensor and the light source is a line-type light source, the term optical planes could also be employed instead of optical axes. In this case, the light plane would correspond to the optical plane of the line-type light source and the detector plane would correspond to the optical plane of the linear sensor.

In one preferred configuration variant, the mounting plane is at least partly formed by a transport device, for example by transport belts. The top sides of said transport belts then predefine the mounting plane for the object.

In one particularly preferred configuration variant of the device according to the invention, the detector, or in particular the linear sensor, is oriented in such a way that its optical axis runs parallel to the normal to the surface of the mounting plane.

In one development of the device according to the invention, this device is configured in such a way that a distance between the parallel straight lines of intersection can be varied. It is thereby possible, in a simple manner, to set the extent to which the detection of directly transmitted light components, and/or singly reflected light components, is avoided.

In one advantageous configuration variant of the device according to the invention, at least one element from a group consisting of the light source and the detector is mounted in movable fashion. In particular, this element is rotatably mounted and/or pivotally mounted. This enables convenient adaptation of the orientation of light source and detector with respect to one another. In one embodiment variant of the invention, in this way the straight lines of intersection of the detector plane and/or light plane with the mounting plane can be oriented parallel to one another in a convenient manner.

Other features which are considered as characteristic for the invention are set forth in the appended claims.

Although the invention is illustrated and described herein as embodied in a method and device for detecting defects in an object, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 4:
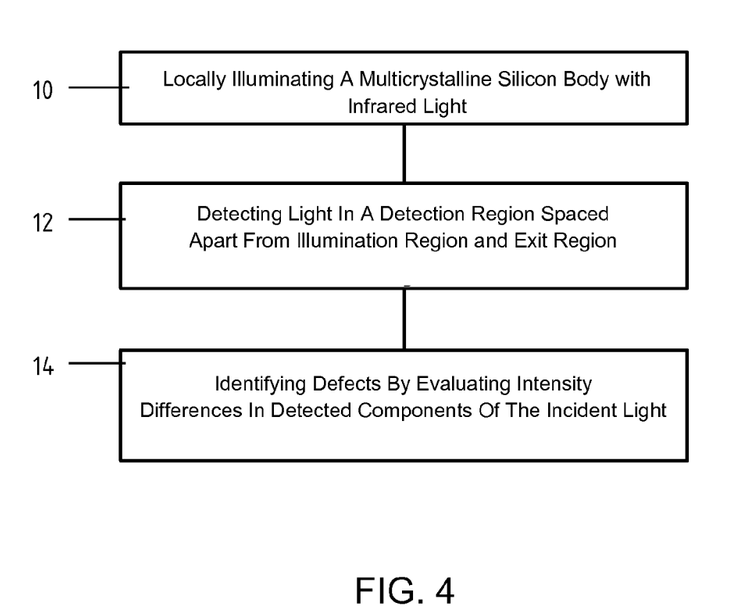
FIG. 4 shows a basic illustration of an exemplary embodiment of the method according to the invention.

FIG. 4 illustrates a first exemplary embodiment of the method according to the invention in schematic illustration. This method involves locally illuminating 10 a multicrystalline silicon body with infrared light. Afterward, light is detected 12 in a detection region spaced apart from an illumination region, in which the silicon body is locally illuminated, and from an exit region of directly transmitted light components of the infrared light incident for the purpose of locally illuminating the silicon body. In this way it is possible largely to prevent the detection of directly transmitted light components of the incident infrared light or singly reflected light components of said infrared light. As has been explained above, defects, in particular breaks or inclusions, leave characteristic intensity differences in the detected components of the incident light, on the basis of which the defects can be identified. Said intensity differences are therefore evaluated and the defects are identified 14 on the basis of them.

Figure 5:
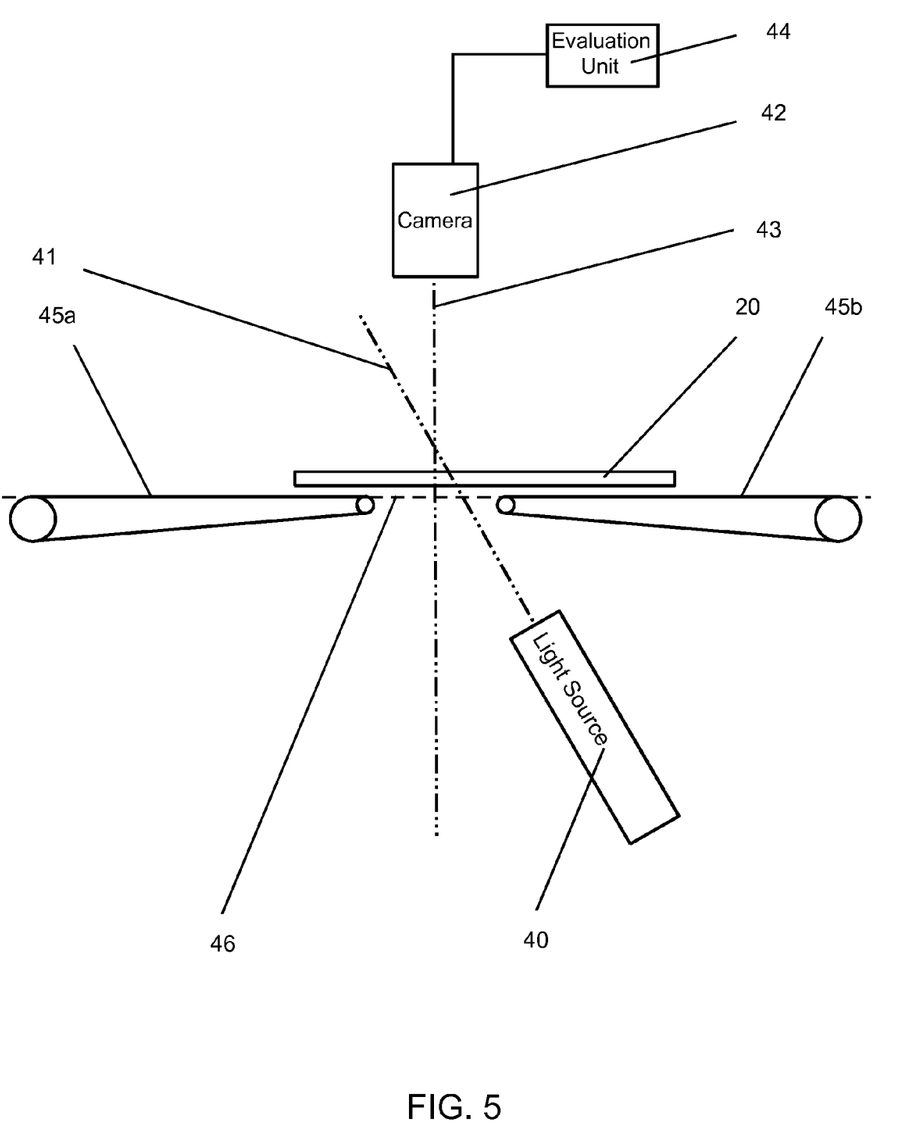
FIG. 5 shows a first exemplary embodiment of a device according to the invention in schematic illustration.

FIG. 5 shows a first exemplary embodiment of a device according to the invention. This device has a light source, which is embodied as a line-type light source 40 in the present case. By means of said light source 40, light is incident on a multicrystalline silicon wafer 20 that has been sawn from a silicon block and overetched acidically. This is illustrated by the optical axis 41 of the line-type light source 40, which, as explained above, can also be regarded as an optical plane. The multicrystalline silicon wafer 20 is mounted on the top sides of transport belts 45a, 45b, which thus form a mounting plane 46. A detector is arranged on an opposite side of the mounting plane 46 relative to the line-type light source 40, said detector being embodied as a line-type camera 42 in the present case. As can be discerned on the basis of the optical axis 43 of said detector, which optical axis could in turn also be regarded as an optical plane, the line-type camera 42 is oriented downward toward the surface of the silicon wafer 20. The reciprocal arrangement of line-type light source 40 and line-type camera 42 with respect to the mounting plane 46 makes it possible to identify defects in the transmitted-light method.

The line-type camera 42 is connected to an evaluation unit 44, which makes it possible to identify defects by evaluating intensity differences in detected components of the incident light.

Figure 6:
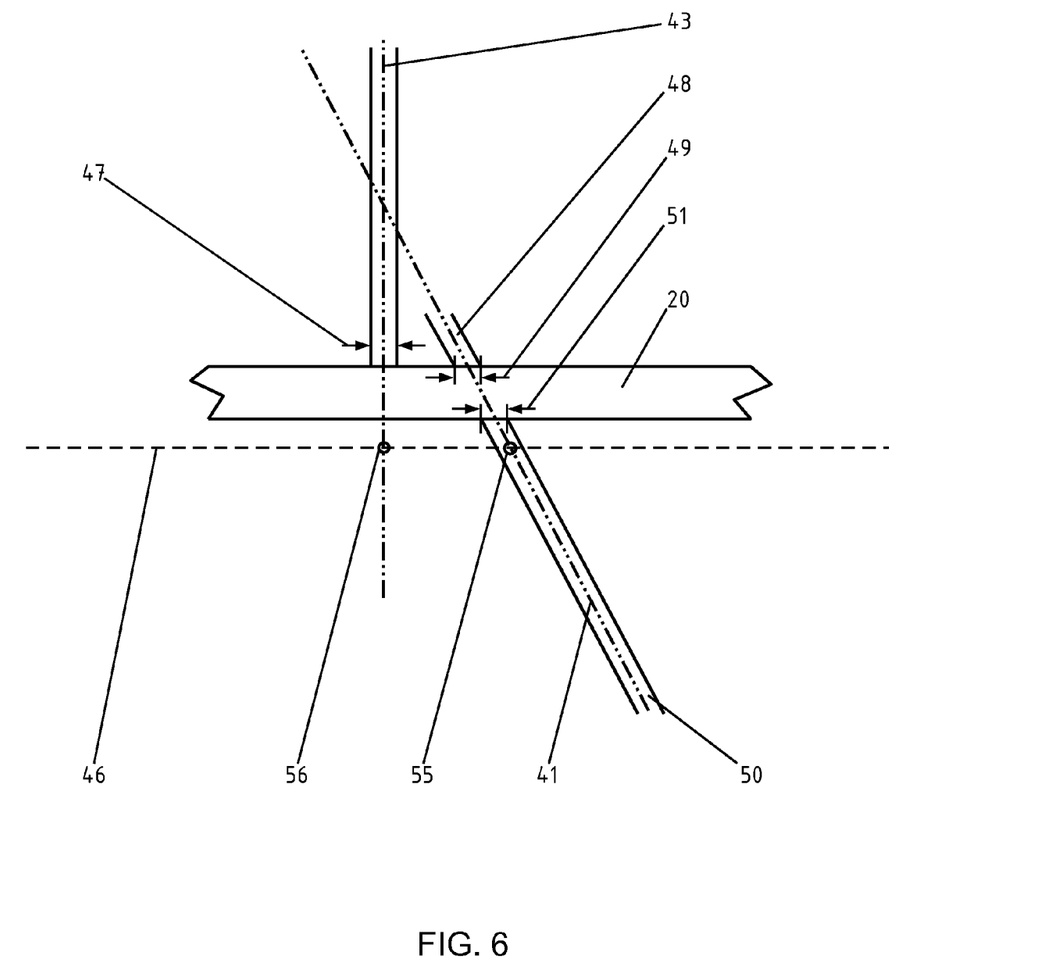
FIG. 6 shows an enlarged illustration of a detail from FIG. 5.

FIG. 6 shows an enlarged partial illustration of the device from FIG. 5 and in this way simultaneously illustrates a method according to the invention which can be carried out by way of the device from FIG. 5. As can be discerned in FIG. 6, light 50 incident from line-type light source 40 along the optical axis 41 impinges on the multicrystalline silicon wafer 20 in an illumination region 51. In this case, the incident light 50 is advantageously focused onto the illumination region 51 by an optical unit provided in the line-type light source 40.

The incident light 50 is partly reflected at the surface of the multicrystalline silicon wafer 20 in the illumination region 51. These singly reflected light components are disregarded in FIG. 6, for the sake of clarity. The remaining light components permeate through the multicrystalline silicon wafer 20 and emerge from the silicon wafer 20 in part at the upper interface of the silicon wafer 20 with respect to the surroundings. These constitute the directly transmitted light components 48. A possible parallel offset of the light emergence on account of refraction of the light at the interfaces is disregarded in all of the figures, for the sake of better clarity.

The remaining, non-directly transmitted light components are reflected at the interface with respect to the surroundings. These singly reflected light components emerge from the silicon wafer 20 in part at the underside thereof and, consequently, can no longer pass into the detector 42. The remaining light components are reflected a second time and thus constitute multiply reflected light components. This reflection process at the interfaces takes place multiply. On account of the oblique incidence of the incident light 50, this results in a propagation of the multiply reflected light toward the left in the illustration in FIG. 6, such that said light ultimately passes into a detection region 47 of the detector and can be detected there after emerging from the silicon wafer 20.

This description of the light courses is simplified and in this way sufficient at best for objects having comparatively smooth surfaces. In the case of the more or less rough surfaces present in reality on the objects to be examined, by contrast, there is more or less arbitrary scattering at the interfaces of the object with respect to the surroundings. Precisely this arbitrary scattering makes the method according to the invention efficient. This is because, by way of example, the incident light 50 can be radiated in genuinely parallel to the optical axis 43 of the line-type camera and it is nevertheless possible to detect light components in the detection region 47. This can be attributed to the fact that, on account of the above-described arbitrary scattering at the surface of the silicon wafer 20, light also propagates in the plane of the silicon wafer, inter alia, which would otherwise not be the case with the assumed genuinely parallel incidence of the incident light 50 with ideally smooth surfaces of the silicon wafer. Nevertheless, however, in the method according to the invention, too, when there is a high degree of scattering of the incident light 50 at the surface of the object, the silicon wafer 20 in the present case, as a result of oblique incidence of the incident light, i.e. as a result of oblique illumination such as is illustrated in FIG. 6 and in FIG. 5, the propagation of light components in the silicon wafer, i.e. horizontally toward the left in the illustrations in FIGS. 5 and 6, is amplified.

The multiple reflection brings about light propagation within the examined object, within the silicon wafer 20 in the present exemplary embodiment, which has good isotropy. In addition light propagation with good homogeneity arises parallel to the illumination region 51 running linearly on account of the use of a line-type light source 40. Since the light propagates within the object and, particularly in the case of silicon, has long free path lengths, the crystal structure of the multicrystalline silicon wafer 20 disappears in the image generated by the line-type camera 42 to an extent that is all the greater, the further the distance between the detection region 47 and the illumination line 49. The image detected by the line-type camera is then determined to an ever greater extent by the surface roughness of the object, the silicon wafer 20 in the present case. In the exemplary embodiment in FIGS. 5 and 6, the silicon wafer 20 has been sawn from a silicon block and thus has great surface roughness. This additionally intensifies the effect of multiple reflection utilized by the method according to the invention.

If there are inclusions or breaks in the examined object, in the silicon wafer 20 in the present exemplary embodiment, then this results in characteristic intensity differences in the detected light components, on the basis of which these defects can be identified with the aid of image processing algorithms in the evaluation unit 44.

As shown in FIG. 6, in the exemplary embodiment illustrated, the detection region 47 of the line-type camera 42 is spaced apart from the illumination region 51 and also from the exit region 49 of directly transmitted light components 48. This makes it possible, in a simple manner, largely to avoid the detection of directly transmitted components 48 of the incident light 50 and the detection of singly reflected components of the incident light 50.

In the exemplary embodiment in FIG. 5, the longitudinal extension directions of the line-type light source 40 and of the line-type camera 42 run perpendicularly to the plane of the drawing. The longitudinal extension direction of the line-type light source 40 and the optical axis 41 thereof thus span a light plane which likewise runs perpendicularly to the plane of the drawing and the position of which in the plane of the drawing is illustrated by the optical axis 41 of the line-type light source 40. Hereinafter, therefore, the reference symbol 41 also serves as a reference for the light plane. Accordingly, the longitudinal extension direction of the line-type camera 42 and the optical axis 43 thereof span a detector plane, which likewise runs perpendicularly to the plane of the drawing and the position of which within the plane of the drawing is represented by the optical axis 43 of the line-type camera. Hereinafter, therefore, the reference symbol 43 is simultaneously used as a reference for said detector plane.

The light plane 41 and the detector plane 43 intersect the mounting plane 46 and in this case form straight lines of intersection 55 and 56, respectively. These straight lines of intersection 55 and 56 run perpendicularly to the plane of the drawing and are oriented parallel to one another.

In the exemplary embodiment in FIG. 5, the line-type light source 40 is mounted in a movable fashion. It is mounted such that it is rotatable about an axis running perpendicularly to the plane of the drawing and, in addition, pivotable about an axis in the plane of the drawing. In this way, the straight lines of intersection 55, 56 can be oriented parallel to one another in a convenient manner. In addition, the distance between the parallel straight lines of intersection 55, 56 can be varied in a simple manner. For this purpose, it is merely necessary to rotate the line-type light source about the axis running perpendicularly to the plane of the drawing. By varying the distance between the parallel straight lines of intersection 55, 56 it is possible, in a convenient manner, to set the extent to which the detection of directly transmitted light components and the detection of singly reflected light components are avoided.

Figure 7:
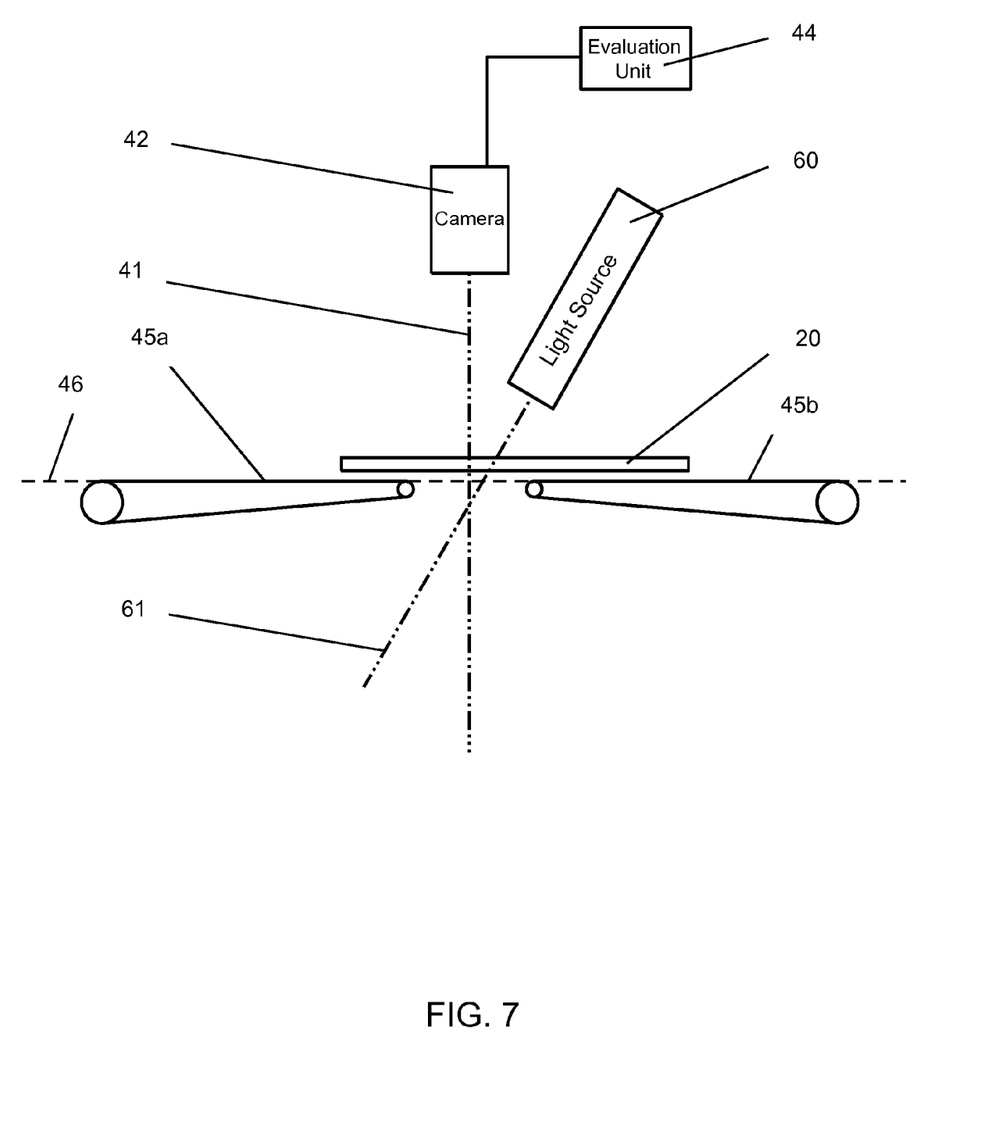
FIG. 7 shows a basic illustration of a second exemplary embodiment of a device according to the invention.

FIG. 7 shows a further exemplary embodiment of a device according to the invention and simultaneously illustrates an exemplary embodiment of the method according to the invention. The device in accordance with FIG. 7 differs from the device known from FIG. 5 merely in terms of the different arrangement of the line-type light sources 60 and 40, respectively, and the resultant consequences for the course of an optical axis 61 of the line-type light source 60 or a light plane 61 of the line-type light source 60.

As can be gathered from FIG. 7, the light source 60 and the detector 42 are arranged on the same side of the mounting plane 46. The illustrated embodiment variant of a device according to the invention is therefore suitable for carrying out reflected-light methods. This is advantageous particularly when a side of the silicon wafer 20 is provided with a coating that is impenetrable to the light used, for example a metal layer. The latter would then have to be arranged on that side of the silicon wafer 20 which faces the transport belts 45a, 45b in the exemplary embodiment in FIG. 7.

The longitudinal extension direction of the line-type light source 60 once again extends perpendicularly to the plane of the drawing in FIG. 7, with the result that the light plane spanned by the longitudinal extension direction of the line-type light source 60 and the optical axis 61 thereof firstly runs perpendicularly to the plane of the drawing and secondly its position within the plane of the drawing is represented by the optical axis 61. Therefore, the reference symbol 61 is simultaneously used as a reference for this light plane.

Figure 8:
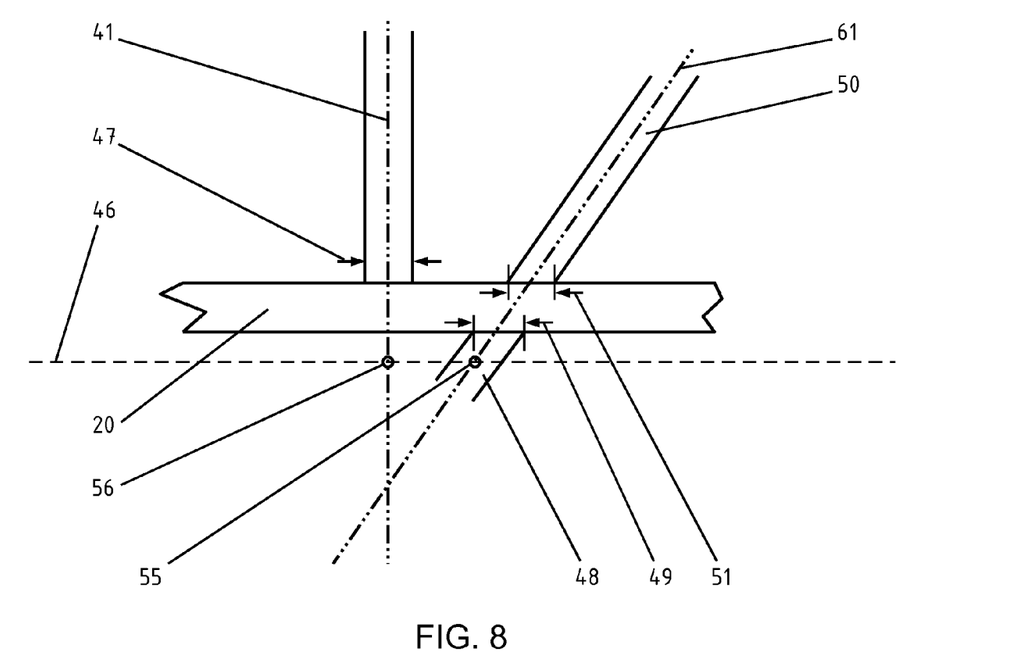
FIG. 8 shows an enlarged illustration of a detail of FIG. 7.

FIG. 8 shows an enlarged partial illustration of FIG. 7. As can be gathered therefrom, in the exemplary embodiment in FIG. 7, too, the detection region 47 of the line-type camera 42 is arranged in a manner spaced apart from the illumination region 51 and also from the exit region 49 of directly transmitted light components 48. As already explained, in this way it is possible, in a simple manner, largely to avoid the detection of directly transmitted light components 48 or singly reflected light components.

Figure 9:
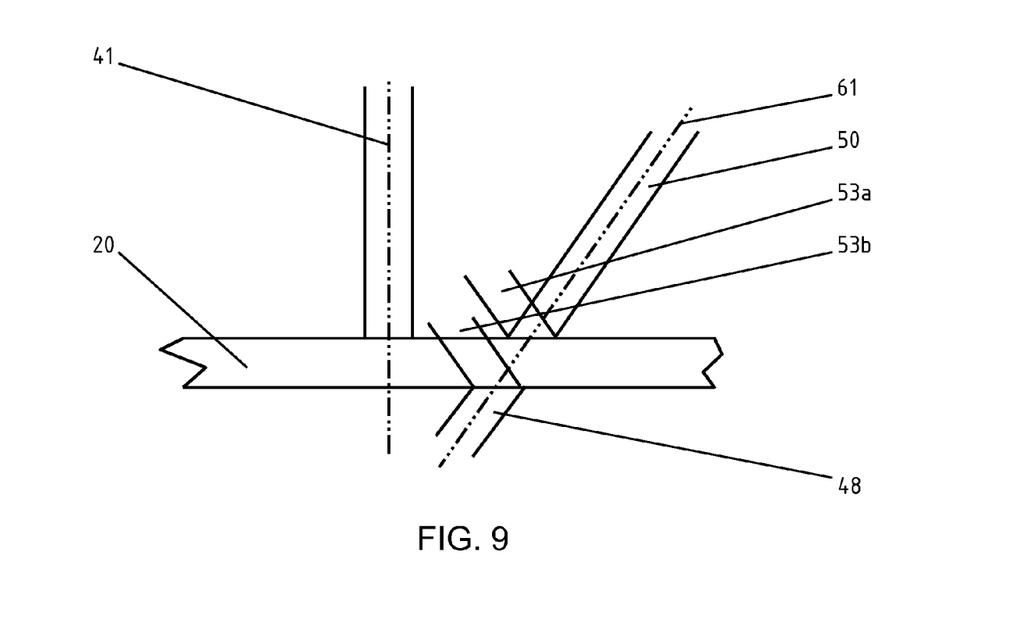
FIG. 9 shows an enlarged illustration of the same partial region as in FIG. 8, but with schematic representation of singly reflected light components.

The fact that the distance between the detection region 47 and the illumination region 51 and/or the exit region 49 influences the degree to which the detection of singly reflected light components is avoided is illustrated in FIG. 9. The latter shows the same enlarged partial illustration as FIG. 8, but singly reflected light components 53a, 53b are additionally represented. On the basis of the latter it becomes clear that, in the case of the distance between the detection region and the exit region 49 as chosen in the present case, the detection of singly reflected light components 53a, 53b is largely avoided. If the detection region 47 is moved closer to the illumination region 51, however, then firstly singly reflected light components 53b are partly detected, and with further movement toward the illumination region 51, singly reflected components 53a are also detected. By contrast, the risk of the detection of directly transmitted light 48 is low in the case of a reflected-light configuration, that is to say in the case where line-type light source 60 and line-type camera 42 are arranged on the same side.

As shown in FIG. 8, the straight lines of intersection 55, 56 of the light plane 61 and of the detector plane 41 again run parallel to one another in the exemplary embodiment in FIG. 7. The line-type light source 60 is once again mounted in movable fashion. In particular, it is embodied such that it is rotatable with respect to an axis running perpendicularly to the plane of the drawing and pivotable relative to an axis running in the plane of the drawing, with the result that line-type light source 60 and line-type camera 42, or the light plane 61 and the detector plane 41, can be oriented relative to one another in a convenient manner. In addition, the distance between the straight lines of intersection 55, 56 can be varied in a convenient manner analogously to the description in connection with FIG. 5.

In one particularly preferred embodiment variant of the device according to the invention, a recording unit for a light source, in particular a line-type camera 40, 60, is provided on both sides of the mounting plane 46, such that the device according to the invention can be operated both in the reflected-light method and in the transmitted-light method. By way of example, the configurations in FIGS. 5 and 7 could thus be realized with the same device.

The invention claimed is:

1. A method for detecting defects in an object, the method which comprises:
   locally illuminating the object by irradiating the object with incident light having a wavelength to which the object is transparent;
   detecting multiply reflected components of the incident light while at least partly avoiding a detection of directly transmitted components of the incident light and at least partly avoiding a detection of singly reflected components of the incident light; and
   identifying defects by evaluating intensity differences in the detected components of the incident light.

2. The method according to claim 1, which comprises detecting defects in inhomogeneous objects.

3. The method according to claim 1, which comprises detecting defects in silicon bodies.

4. The method according to claim 3, which comprises detecting defects in silicon wafers.

5. The method according to claim 3, which comprises detecting defects in silicon bodies that have been sawed from a starting silicon body.

6. The method according to claim 1, which comprises detecting the multiply reflected components of the incident light while completely avoiding the detection of directly transmitted components of the incident light and completely avoiding the detection of singly reflected components of the incident light.

7. The method according to claim 1, which comprises, for the purpose of detecting multiply reflected components of the incident light while at least partly avoiding the detection of directly transmitted components of the incident light and while at least partly avoiding the detection of singly reflected components of the incident light, detecting light in a detection region that is spaced apart from a locally irradiated illumination region of the object and from an exit region of directly transmitted light components.

8. The method according to claim 1, wherein the step of locally illuminating comprises irradiating a part of a given side of the object, and wherein multiply reflected components of the incident light are detected on the same given side of the object.

9. The method according to claim 1, wherein the step of locally illuminating comprises irradiating a part of a first side of the object, and wherein multiply reflected components of the incident light are detected on a second side, opposite from the first side of the object.

10. A device for detecting defects in an object, the device comprising:
    a light source for locally illuminating the object with light having a wavelength to which the object is transparent; and
    a detector for detecting light emitted by said light source;
    wherein said detector and said light source are arranged such that at least one part of an illumination region in which the object can be locally illuminated by said light source and also at least one part of an exit region of directly transmitted light components lie outside a detection region of the detector.

11. The device according to claim 10, configured to carry out the method according to claim 1.

12. A device for carrying out the method according to claim 1, comprising:
    a light source for locally illuminating an object with light having a wavelength to which the object is transparent; and
    a detector for detecting light emitted by said light source; and
    wherein said detector and said light source are disposed such that at least one part of an illumination region in which the object can be locally illuminated by way of said light source and also at least one part of an exit region of directly transmitted light components lie outside a detection region of said detector.

13. The device according to claim 12, wherein the detection region of said detector is spaced apart from the illumination region and from the exit region of the directly transmitted light components.

14. The device according to claim 12, wherein said light source and said detector are commonly disposed on a same side of a mounting plane in which the object can be mounted.

15. The device according to claim 12, wherein said light source and said detector are disposed on mutually opposite sides of a mounting plane in which the object can be mounted.

16. The device according to claim 12, wherein said light source is at least one line-type light source and said detector is at least one device with a linear sensor.

17. The device according to claim 16, wherein said line-type light source and said linear sensor are oriented such that a light plane spanned by a longitudinal extension direction of said light source and an optical axis thereof and a detector plane spanned by a longitudinal extension direction of said linear sensor and the optical axis thereof respectively form straight lines of intersection with the mounting plane, and wherein said straight lines of intersection are oriented parallel to one another.

18. The device according to claim 17, wherein a distance between the parallel straight lines of intersection is a variable distance.

19. The device according to claim 12, wherein one or both of said light source and said detector are movably mounted.

20. A device for detecting defects in an object, the device comprising:
- a line-type light source for locally illuminating the object by irradiating the object with incident light having a wavelength to which the object is transparent;
- a detector having a linear sensor for detecting light emitted by said line-type light source;
- said detector being configured for detecting multiply reflected components of the incident light while at least partly avoiding a detection of directly transmitted components of the incident light and at least partly avoiding a detection of singly reflected components of the incident light; and
- an evaluation unit connected to said detector for evaluating intensity differences in the detected components of the incident light and to thereby identify defects in the object.

* * * * *